United States Patent
Yastrebov

(12) 
(10) Patent No.: US 7,214,199 B1
(45) Date of Patent: May 8, 2007

(54) URINE ANALYSIS COLLECTION KIT FOR VETERINARY USE

(75) Inventor: Loretta Yastrebov, Ambler, PA (US)

(73) Assignee: B. Well Veterinary Products, Inc., Maple Glen, PA (US)

( * ) Notice: Subject to any disclaimer, the term of this patent is extended or adjusted under 35 U.S.C. 154(b) by 0 days.

(21) Appl. No.: 11/392,860

(22) Filed: Mar. 29, 2006

(51) Int. Cl.
*A61B 5/00* (2006.01)
*B65D 81/00* (2006.01)
*A61M 1/00* (2006.01)

(52) U.S. Cl. .................. 600/573; 600/576; 600/579; 604/318; 604/324; 604/322; 604/317

(58) Field of Classification Search ............. 600/573, 600/576, 579; 604/318, 324, 317, 322
See application file for complete search history.

(56) References Cited

U.S. PATENT DOCUMENTS 3,625,654 A * 12/1971 Van Duyne ................ 422/102
4,476,879 A * 10/1984 Jackson ..................... 600/573
5,060,317 A * 10/1991 Bertelsen .................... 4/144.2
5,487,393 A * 1/1996 Haswell et al. ............ 600/573
5,738,047 A * 4/1998 McNamara ................. 119/869
6,186,946 B1 * 2/2001 Nakajima ................... 600/362
6,709,409 B2 * 3/2004 Vella ......................... 600/573
2004/0267158 A1* 12/2004 Paasch et al. .............. 600/573
2006/0149164 A1* 7/2006 Lee et al. ................... 600/573

* cited by examiner

*Primary Examiner*—Max F. Hindenburg
*Assistant Examiner*—Jeffrey G. Hoekstra
(74) *Attorney, Agent, or Firm*—Eugene E. Renz, Jr.

(57) ABSTRACT

A system for collecting urine specimens from pet or animal comprising an elongated tray section having at one end a collection chamber for collecting a predetermined volume of urine in fluid communication with an open section of said tray to receive a stream of urine from the pet or animal, a discharge port at the opposite end of said tray and a specimen vial removably mounted to the discharge end of said tray whereby when an animal is urinating, the device is positioned under the stream with the collection chamber end downwardly inclined so that a sufficient quantity flows into the collection chamber to predetermined level and then tilting the device in a reverse direction so the collected sample flows into the specimen vial and is sealed.

5 Claims, 4 Drawing Sheets

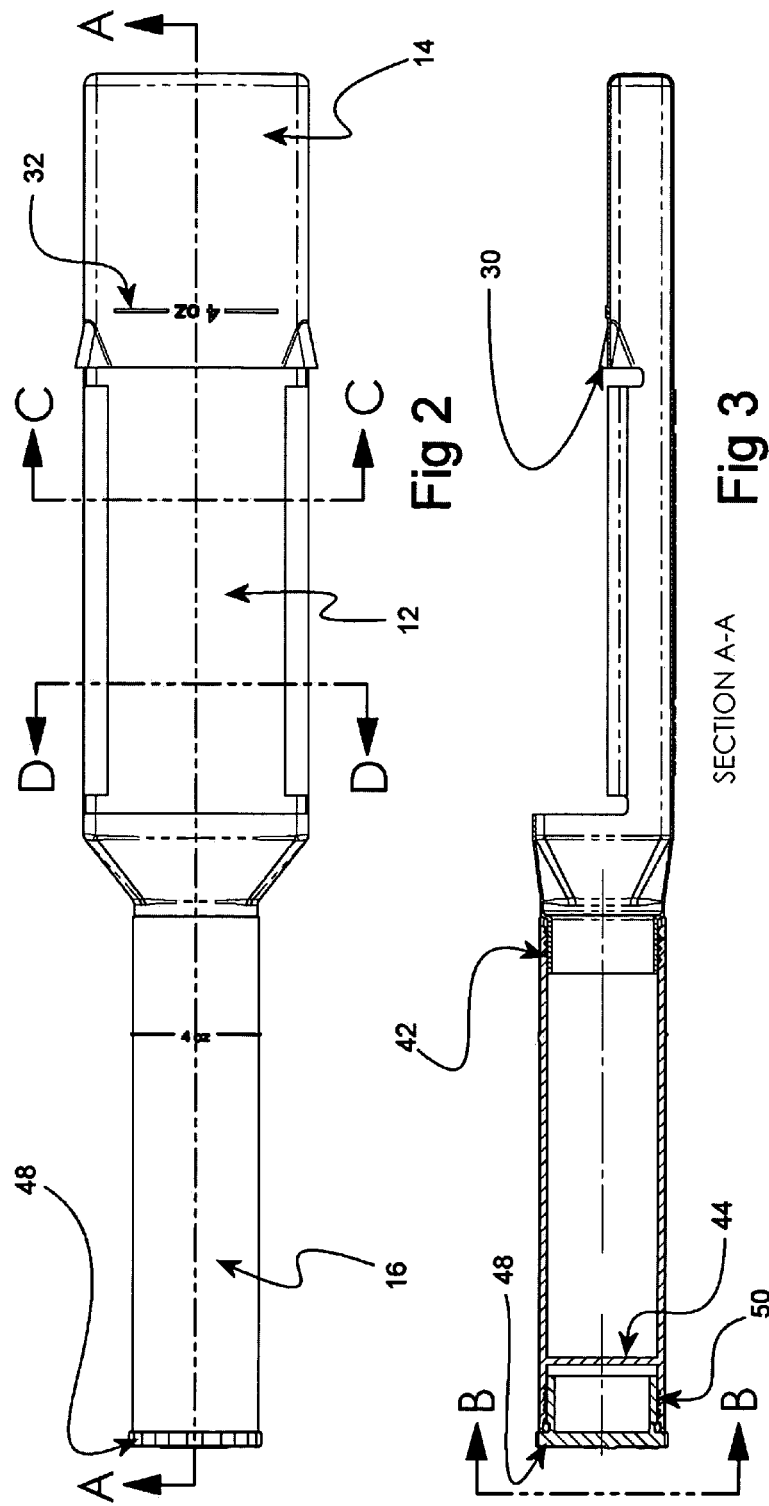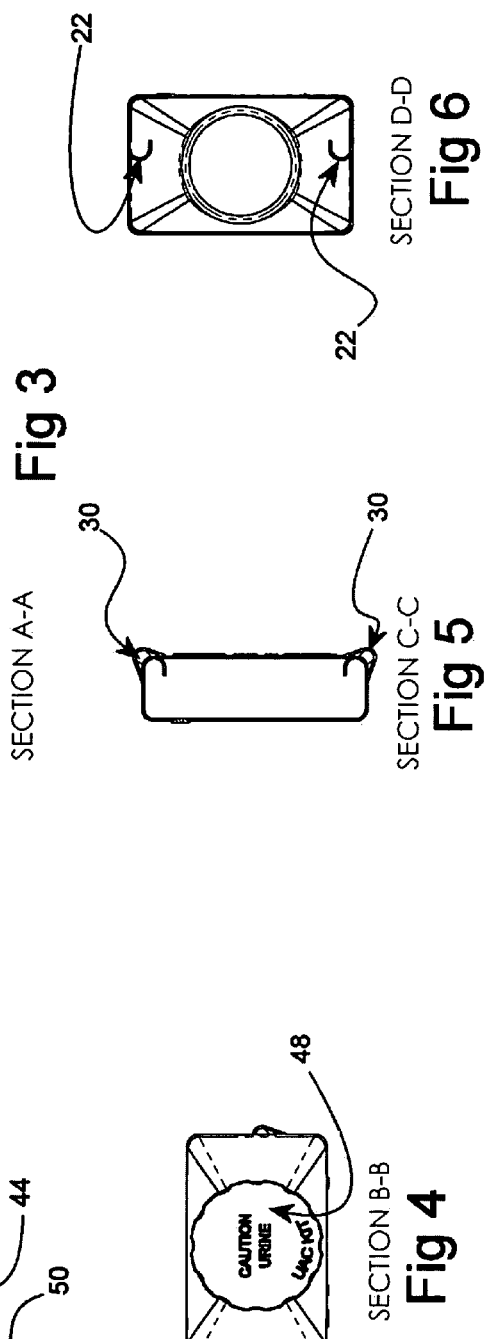

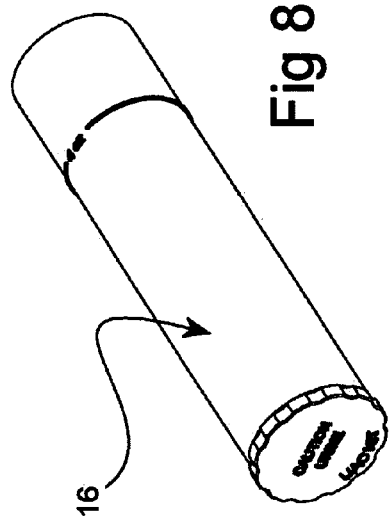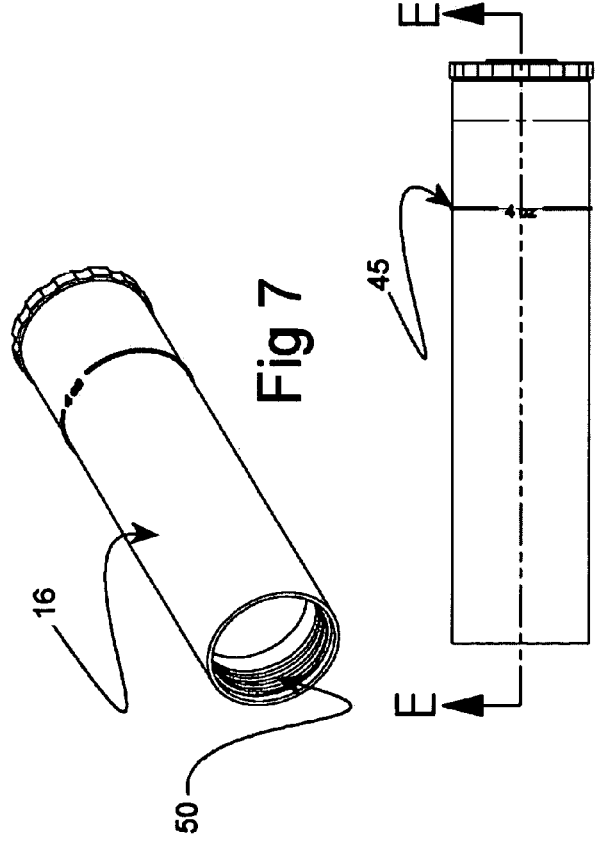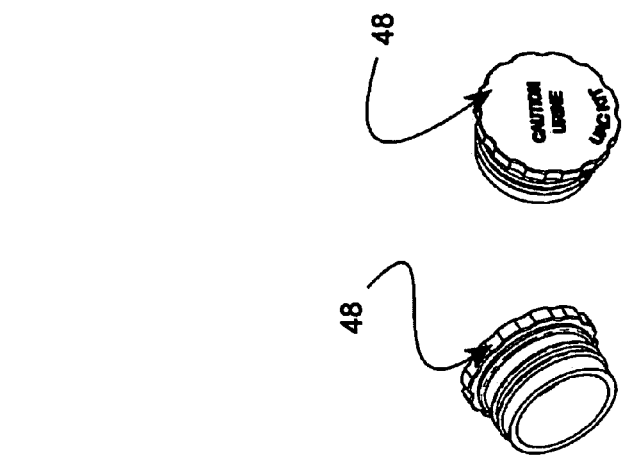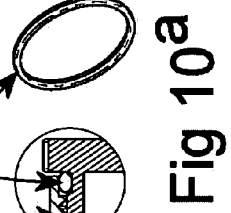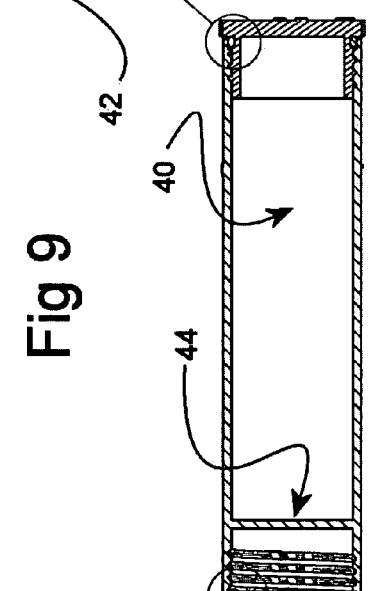

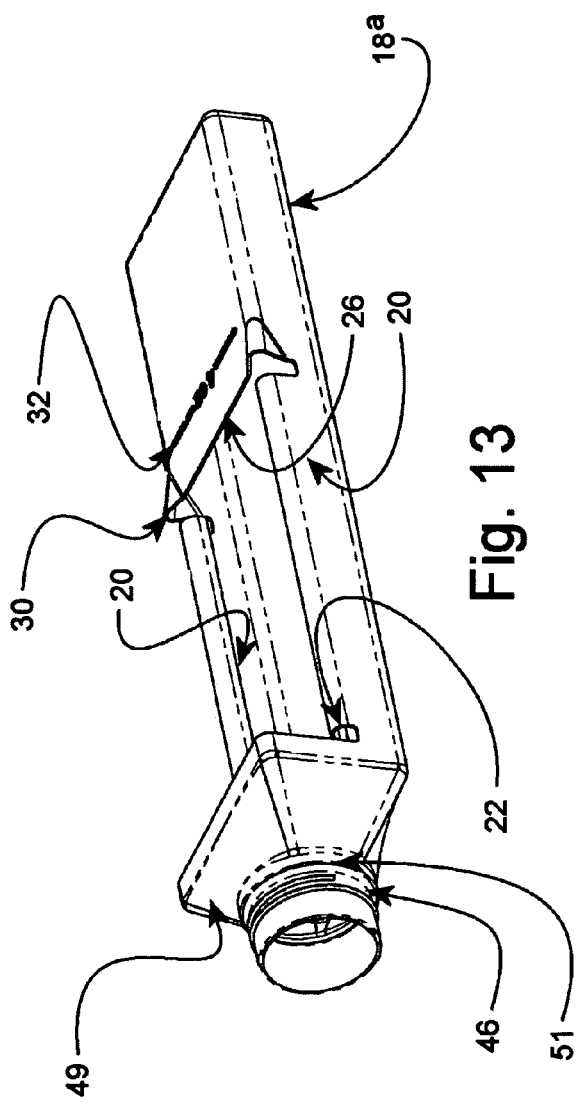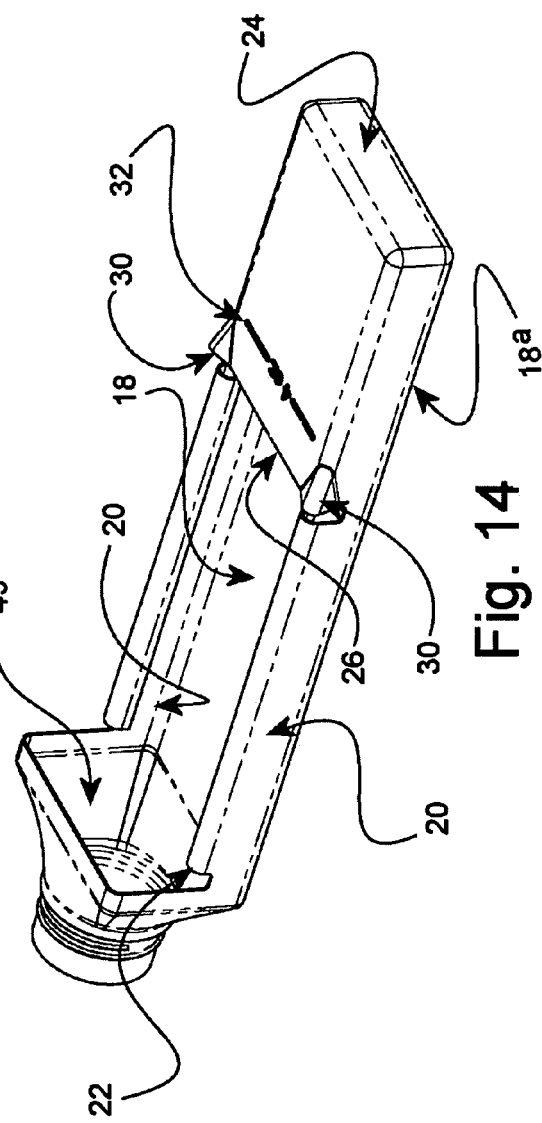

URINE ANALYSIS COLLECTION KIT FOR VETERINARY USE

FIELD OF THE INVENTION

The present invention relates to improvements in devices for collecting "untainted" urine specimens from pets or animal. The novel feature of this construction, allows the user to easily facilitate the collection of a urine sample from their pet or animal in a specimen tray having a chamber for collecting and measuring the desired volume of the urine specimen, then to transferred to a collection vial in a manner avoiding contamination of the specimen. The collected specimen will enable the veterinarian in diagnosing unlimited medical conditions or diseases present in the pet or animal.

BACKGROUND OF THE INVENTION

Specimen collecting devices in the veterinary field are not new per se. The patents listed below show devices for veterinary use in collecting and analyzing fecal matter of animals.

| | | |
|---|---|---|
| GREENWALD | FECAL EXAMINATION DEVICE | 3,819,045 |
| STUDER | FECAL EXAMINATION DEVICE | 3,936,373 |
| COTEY | OVA DETECTOR ASSEMBLY | 4,225,423 |

These prior art devices are designed and configured to produce separation of the ova from the remainder of the matter for analysis. Thus Struder '373 shows an elongated thimble like unit which fits in a cylindrical container for a predetermined quantity of fecal matter to be analyzed.

A flotation liquid is added to the container and thoroughly mixed with the fecal matter specimen. The thimble is now inserted into the container and settles by its own weight into the fecal-liquid mixture. Ova separates from the mixture and flows through perforations to the inside of the thimble. The container is filled with additional liquid to form a slight meniscus. Ova migrate to the meniscus and to a microscope cover glass positioned over the meniscus surface to pick up surface liquid and entrained ova.

Greenwald '045 patent and Cotey '423 patent employ similar devices and systems for floating ova from fecal matter specimens for examination.

Even though these devices and systems are suitable for the purposes intended, they do not have the capability to handle and process urine specimens and do not disclose or suggest a system and device for accumulating a specimen for analysis comparable to the system and device of the present invention.

SUMMARY OF THE INVENTION

The present invention provides a novel device for collection of a urine sample in a container of relatively simplified construction which can be manufactured and assembled easily and economically and which is fully effective for the purposes intended, namely, obtaining an untainted urine specimen from a pet or animal to assist a veterinarian in diagnosing a medical problem of the pet or animal. Thus, the device is comprised of an elongated collection tray having a urine collection chamber at one end, and an open target trough section in fluid communication with the open end of the specimen collection chamber. In the embodiment illustrated, the collection chamber is of generally rectangular shaped cross section comprising an elongated generally rectangular panel forming a common base for the collection chamber and the open trough like collection tray. The collection chamber and trough like collection tray have common rectangular side walls. The collection chamber has an end wall to define a cup like chamber. The front end of the collecting tray has a transfer funnel which tapers inwardly to define an externally threaded cylindrical collar for mounting an elongated generally cylindrical or tubular specimen vial which has internal threads at one end to mount on the threaded collar.

The specimen vial has a bottom wall spaced inwardly from one axial end of the vial remote from the opposing open end which normally is connected to the collar of the collection tray and is internally threaded to removably mount a cap which can be threaded to seal the open end of the specimen vial when filled with a specimen in the manner described below.

Consider now briefly use of the urine collection system of the present invention and assume the parts are assembled as shown in FIG. 3. The user grips the device by the vial when the pet or animal is urinating and approaches from behind for a female and from the side for the male and places the device with the open trough facing up under the urine stream until the collection chamber is filled At this point, the user withdraws the device and tilts it downwardly to fill the chamber to the four (4) ounce indicia mark. Excess urine can be drained through the overflow funnels by gently titling the device.

With the precise urine sample now in the collection chamber, the user slowly tilts the device back so that urine flows rearwardly through the tapered transfer funnel into the specimen vial. With the vial in a vertical position, open end up, the user slowly unscrews specimen collecting tray from the specimen vial. The cap is unscrewed from the bottom end of specimen vial and tightly threaded in the open end of the vial to seal the vial to contamination and leakage. Note that the collar threads into the open end of the specimen vial to avoid dripping of urine which could occur if the collar threaded over the outside of the specimen vial.

DESCRIPTION OF THE DRAWINGS

These and other objects of the present invention and the various features of the details and operation thereof are hereinafter fully set forth with reference to the accompanying drawings, wherein;

FIG. 2 is a top plan view of the specimen collection system and device;

FIG. 3 is a side elevational view of the specimen collection system and device of the present invention partly in section so that the internal construction can be seen more readily;

FIG. 4 is an end elevational view of the handle end of the device as viewed along lines B—B of FIG. 3;

FIG. 5 is a transverse sectional view taken on lines C—C of FIG. 2 showing details of the drain off channels in the urine collection chamber of the device;

FIG. 6 is another transverse view taken along lines D—D of FIG. 2;

FIGS. 7 and 8 are perspective views of the collection vial showing the closure cap before sealing (FIG. 7) and after sealing the urine specimen (FIG. 8);

FIG. 9 is a side elevational view of the sealed specimen vial;

FIG. 10 is a longitudinal sectional view taken on lines E—E of FIG. 9;

FIGS. 10a and 10b are fragmentary sectional views of the portions circled in FIG. 10 showing the thread and seal details for mounting the closure cap at opposing ends of the collection vial;

FIGS. 11 and 12 are perspective view of the closure cap; and

FIGS. 13 and 14 are perspective views of the specimen collection tray with the specimen vial removed.

DESCRIPTION OF THE PREFERRED EMBODIMENT

Figure 1:
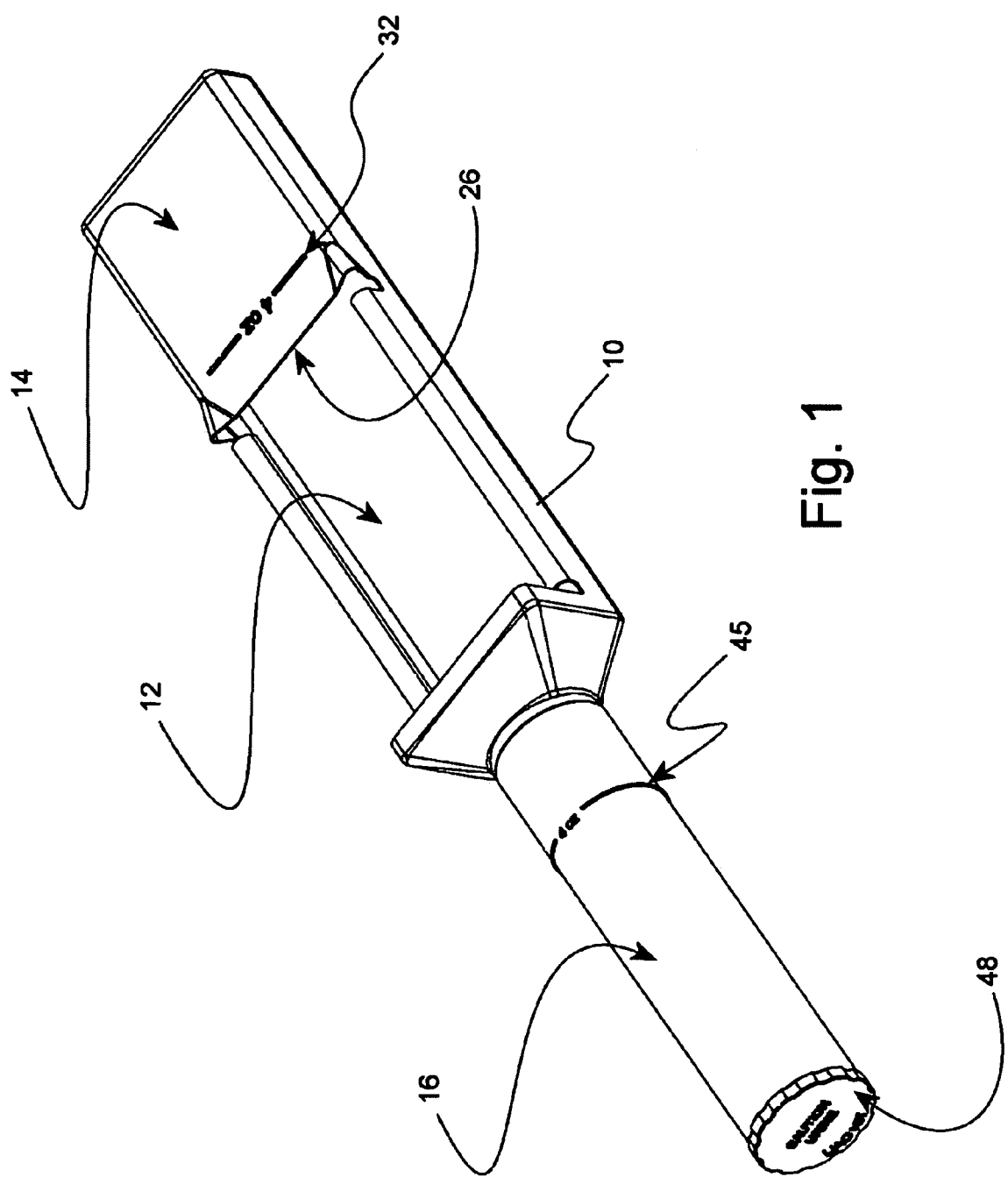
FIG. 1 is a perspective view of system and device for collecting urine specimen for animals in accordance with the present invention.

Referring now to the drawings and particularly to FIGS. 1–3 thereof there is shown a urine analysis collection device in accordance with the present invention generally designated by the numeral 10. The device may be made of a moldable plastic material, preferably a clear plastic material. Considering first the broad structural details and arrangement, the device 10 comprises a specimen collection tray 12 having a collection chamber 14 at one end for measuring a predetermined volume of urine specimen and a specimen vial 16 detachably mounted at the opposite end of the collection tray 12 which functions as a handle when the device is used to obtain a urine specimen from an animal.

The device is used to accumulate a sample by holding the device by the specimen vial 16 and positioning the open tray 12 in the path of the urine stream when the animal is urinating and the collection chamber 14 tilted downwardly. When a suitable quantity has been collected, the user simply tilts the device rearwardly so that the collected sample flows through the transfer funnel into the specimen vial 16 and then sealed with a cap. The user then prints name of pet or animal and date on the vial and delivers to the veterinarian.

Considering now more specifically the structural details and arrangement of the urine collection device of the present invention and with reference to FIGS. 13–14, the tray 12 has a generally rectangular base 18, upstanding side walls 20,20, projecting upwardly from opposing elongated side edges 18a, 18a of the base 18. As illustrated the side walls 20,20 have a generally curved arcuate upper edge 22,22 extending approximately the length of the open portion of the tray 12 which function as stiffeners and present a smooth finishing surface to preclude injury to the animal and user. The curved edges 22,22 extend inwardly and prevent spillage if the tray is tilted slightly during accumulation of a urine specimen.

The measuring and specimen collection chamber 14 is defined by an end wall 24 extending upwardly from the base 18 forming the bottom of the collection chamber 14. The collection chamber 14 has a generally rectangular top panel 26 formed intergrally with the end wall 24 and side walls 20,20. The walls defining the chamber 14 are sized so that the volume of the collection chamber 14 is slightly greater than 4 oz. the preferred specimen size. Outwardly flared funnels 30 are formed at the top corners of the open end of the collection chamber 14 to provide overflow outlets for draining excess urine in the collection chamber 14. Note the top panel 26 has a volume indicia line 32 to provide visual aid in controlling volume of the specimen to the optimum 4 oz. volume.

The end of the tray 12 opposite the collection chamber 14 has a transfer funnel 36 comprising a peripheral end wall which tapers outwardly and downwardly and merges with a hollow collar 38 having external screw threads 46 to detachably or removably mount the specimen vial 16.

The specimen vial 16 as best illustrated in FIGS. 3 and 7–10 inclusive comprises an elongated, hollow tubular housing 40 having internal screw threads 42 at its open end complementing the collar threads 46 to normally mount on the collar 38 of the collection tray 12. The opposite end of the specimen vial 16 has a bottom closure wall 44 spaced axially inwardly a predetermined distance and is internally threaded as at 50 for mounting a closure cap 48 having complementary threads 52. The cap 48 is used to seal the specimen vial 16 after it is filled with a specimen and disengaged from the collecting tray in the manner described.

Recapping use of the urine collection system of the present invention, the parts comprising the device are sealed in a package under sterile conditions. The parts are assembled together in the manner shown in FIGS. 1–3 inclusive. When the pet or animal is ready to deliver a urine specimen, the user simply unseals the package, grasps the device by the handle (specimen vial 16) and positions it with the open tray in the path of the urine stream and tilted slightly downwardly so that urine flows into the collection chamber 14. When a suitable quantity has accumulated as measured by the 4 oz. measuring line 32, the device is withdrawn and tilted to reverse flow in the collecting tray 12 to fill the specimen vial 16. With the device now in a vertical position, the user carefully unthreads the specimen vial 16 from the tray 12, removes the cap 48 from the bottom of the specimen vial 16 and seals the open end of the vial 16. The user enters the pertinent data on the vial and sends to veterinarian. After use, the tray should be disposed of immediately to avoid any subsequent use which could cause contamination.

Even though particular embodiments of the invention have been illustrated and described herein, it is not intended to limit the invention and changes and modifications may be made therein within the scope of the attached claims. For example, even though the tray is of a generally rectangular shape, the tray and collection chamber may be of other geometric shapes or configuration. Further, the vial may be of a shape other than tubular and circular to provide for example a better hand grip for use of the device. It is also the case that the cap and vial may be detachably connected by a press fit rather than threads.

What is claimed is:

1. A device for collecting a urine specimen from an animal, comprising: an elongated open tray having a bottom wall and upstanding sidewalls extending from opposing side edges of the bottom wall, a top wall overlying and spaced from said bottom wall defining a specimen collection chamber formed integrally with the tray and extending from one end thereof and having an open upper end to provide fluid communication between the collection chamber and tray, a means for accumulating a predetermined volume of urine specimen in said collection chamber, a hollow elongated funnel at the opposite end of said tray with respect to the collection chamber and formed integrally therewith, and a means for detachably mounting a sealable urine specimen collection tube formed integrally with the tray, whereby tilting of the device forwardly fills the collection chamber with a predetermined volume of urine specimen and thereafter when the device is titled readwardly the predetermined volume of specimen flows directly into the sealable urine collection tube.

2. A device for collecting a urine specimen from an animal, comprising, an elongated open tray having a bottom wall and upstanding sidewalls extending from opposing side edges of the bottom wall, a top wall overlying and spaced from said bottom wall defining a specimen collection chamber formed integrally with the tray and extending from one end thereof and having an open upper end to provide fluid communication between the collection chamber and tray, a means for accumulating a predetermined volume of urine specimen in said collection chamber, outwardly angled funnels at corners of the container adjacent the juncture of the collection chamber and tray to direct a flow of excess urine when needed, a hollow elongated funnel at the opposite end of said tray with respect to the collection chamber and formed integrally therewith, and a means for detachably mounting a sealable urine collection tube formed integrally with the tray, whereby tilting of the device forwardly fills the collection chamber with a predetermined volume of specimen and thereafter when the device is tinted readwardly the predetermined volume of specimen flows directly into the sealable urine collection tube.

3. A device for collecting a urine specimen from an animal comprising an elongated open tray having a bottom wall and upstanding sidewalls extending from opposing side edges of the bottom wall, a top wall overlying and spaced from said bottom wall defining a specimen collection chamber formed integrally with the tray and extending from one end thereof and having an open upper end to provide fluid communication between the collection chamber and tray, outwardly angled funnels at corners of the collection chamber adjacent the juncture of the collection chamber and tray to direct a flow of excess urine when needed, a hollow elongated funnel at the opposite end of said tray with respect to the collection chamber and formed integrally therewith, and a means for detachably mounting a urine collection tube formed integrally with the tray, wherein the upper edge of the sidewalls of the tray are curved inwardly to present a smooth surface to prevent injury to the animal and to contain spillage.

4. A device for collecting a urine specimen from an animal, comprising: an elongated open tray having a bottom wall and upstanding sidewalls extending from opposing side edges of the bottom wall, a top wall overlying and spaced from said bottom wall defining a specimen collection chamber formed integrally with the tray and extending from one end thereof and having an open upper end to provide fluid communication between the collection chamber and tray, outwardly angled funnels at corners of the collection chamber adjacent the juncture of the collection chamber and tray to direct a flow of excess urine when needed to facilitate collection of a predetermined volume of urine specimen, a hollow elongated funnel at the opposite end of said tray with respect to the collection chamber and, formed integrally therewith, and a means for detachably mounting a urine collection tube formed integrally with the tray, wherein the upper edge of the sidewalls of the tray are curved inwardly to present a smooth surface to prevent injury to the animal and to contain spillage, said specimen collection tube is detachably mounted by a threaded connection at the open end to said funnel and mounted with a threaded closure cap at its opposite closed end to seal the collection tube when a urine specimen is accumulated.

5. A device as claimed in claim 4, wherein the specimen collection tube has a bottom opposite the intentionally the added open end and is spaced upwardly from the lower end which is internally threaded for mounting a closure cap used to seal the collection tube after it is filled with a urine specimen.

* * * * *

UNITED STATES PATENT AND TRADEMARK OFFICE
CERTIFICATE OF CORRECTION

PATENT NO. : 7,214,199 B1 Page 1 of 1
APPLICATION NO. : 11/392860
DATED : May 8, 2007
INVENTOR(S) : Loretta Yasterbov It is certified that error appears in the above-identified patent and that said Letters Patent is hereby corrected as shown below:

On the Title Page, Item (73) Assignee B. Well Veterinary Products, Inc., Maple Glen, PA (US) is deleted from the issued patent.

Signed and Sealed this

Second Day of December, 2008

JON W. DUDAS
*Director of the United States Patent and Trademark Office*